United States Patent
Ryan

(10) Patent No.: US 8,615,408 B2
(45) Date of Patent: Dec. 24, 2013

(54) INTERACTIVE PATIENT FORUMS

(75) Inventor: John C. Ryan, Boston, MA (US)

(73) Assignee: Koninklijke Philips N.V., Eindhoven (NL)

( * ) Notice: Subject to any disclaimer, the term of this patent is extended or adjusted under 35 U.S.C. 154(b) by 573 days.

(21) Appl. No.: 12/524,222

(22) PCT Filed: Jan. 25, 2008

(86) PCT No.: PCT/IB2008/050277
§ 371 (c)(1),
(2), (4) Date: Jul. 23, 2009

(87) PCT Pub. No.: WO2008/093270
PCT Pub. Date: Aug. 7, 2008

(65) Prior Publication Data
US 2009/0326979 A1    Dec. 31, 2009

Related U.S. Application Data

(60) Provisional application No. 60/887,822, filed on Feb. 2, 2007.

(51) Int. Cl.
G06Q 50/00    (2012.01)
H04N 7/16     (2011.01)
H04N 7/14     (2006.01)

(52) U.S. Cl.
USPC ............................. 705/2; 725/25; 348/14.08

(58) Field of Classification Search
USPC ........................................................ 705/2, 3
See application file for complete search history.

(56) References Cited

U.S. PATENT DOCUMENTS

| | | | |
|---|---|---|---|
| 5,689,641 A * | 11/1997 | Ludwig et al. | 709/241 |
| 5,764,901 A * | 6/1998 | Skarbo et al. | 709/204 |
| 5,879,163 A | 3/1999 | Brown et al. | |
| 5,887,133 A | 3/1999 | Brown et al. | |
| 5,897,493 A | 4/1999 | Brown | |
| 5,960,403 A | 9/1999 | Brown | |
| 5,997,476 A | 12/1999 | Brown | |
| 6,014,432 A | 1/2000 | Modney | |
| 6,039,688 A * | 3/2000 | Douglas et al. | 600/300 |
| 6,101,478 A | 8/2000 | Brown | |
| 6,168,563 B1 | 1/2001 | Brown | |

(Continued)

FOREIGN PATENT DOCUMENTS

| | | |
|---|---|---|
| EP | 1617361 A1 | 1/2006 |
| WO | 9712544 A1 | 4/1997 |

(Continued)

OTHER PUBLICATIONS

Pappas, Charles; "Get the Message." Dec. 1999, Home Office Computing, pp. 17 , 12 , 41.*

(Continued)

Primary Examiner — Rachel L Porter

(57) ABSTRACT

In a medical communication method, two or more persons are identified as having a selected medical condition or characteristic. At the residence of each identified person, a video conference-enabling unit (56) is operatively connected with a consumer electronics device (50, 52) disposed in the identified person's residence. A video conference is conducted between at least two of the two or more identified persons using their respective consumer electronics devices (50, 52) and video conference-enabling units (56).

7 Claims, 15 Drawing Sheets

(56) References Cited

U.S. PATENT DOCUMENTS

Figure 1:
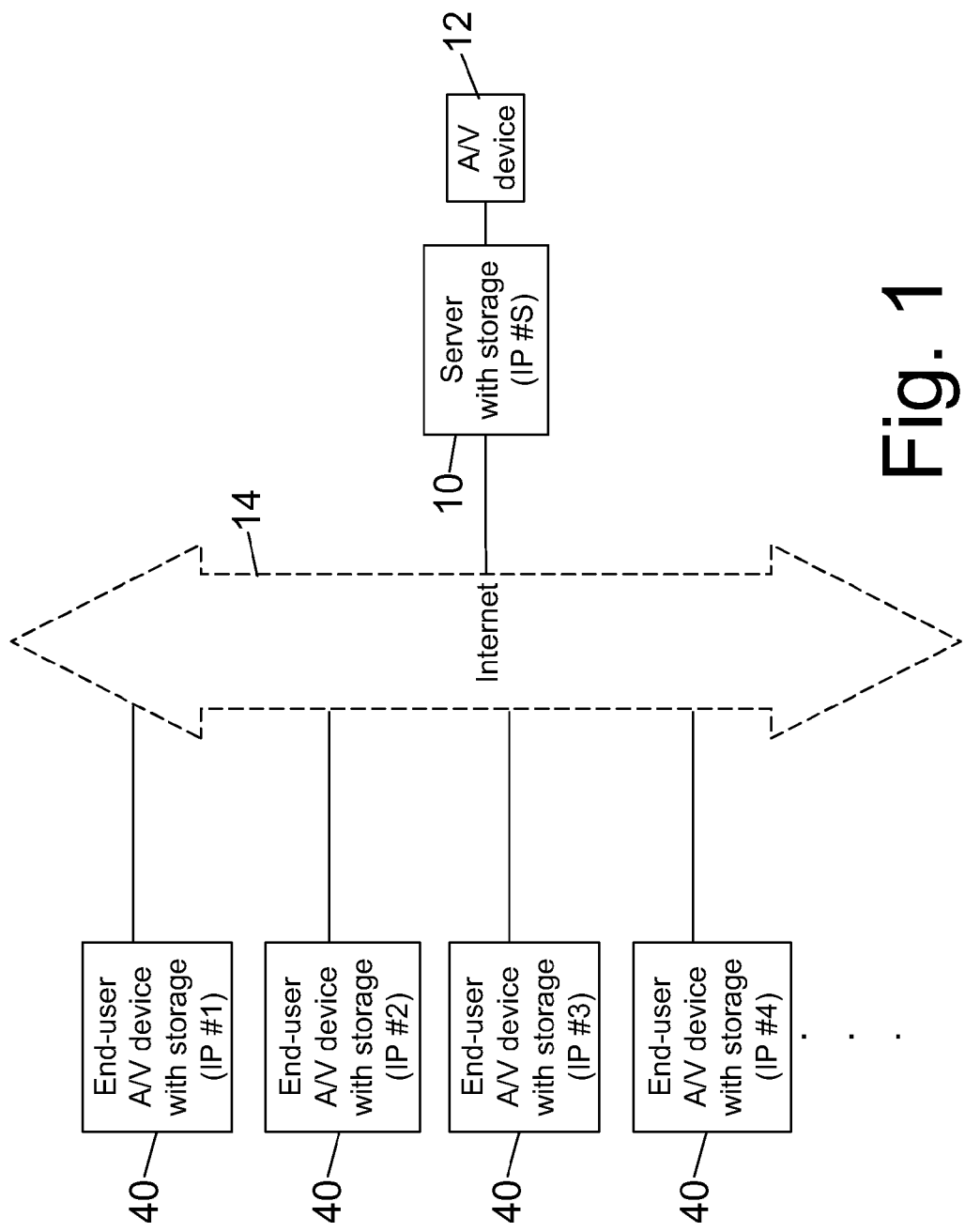

| | | | |
|---|---|---|---|
| 6,248,065 B1 | 6/2001 | Brown | |
| 6,290,646 B1 | 9/2001 | Cosentino et al. | |
| 6,375,469 B1 | 4/2002 | Brown | |
| 6,454,705 B1 | 9/2002 | Cosentino et al. | |
| 6,515,705 B1* | 2/2003 | Fumio et al. | 348/375 |
| 6,535,207 B1* | 3/2003 | Hiroki | 345/207 |
| 6,723,045 B2 | 4/2004 | Cosentino et al. | |
| 6,755,783 B2 | 6/2004 | Cosentino et al. | |
| 6,968,375 B1 | 11/2005 | Brown | |
| 2001/0052019 A1 | 12/2001 | Walters et al. | |
| 2002/0116221 A1 | 8/2002 | Fields et al. | |
| 2002/0133377 A1 | 9/2002 | Brown | |
| 2002/0186243 A1 | 12/2002 | Ellis et al. | |
| 2003/0069753 A1 | 4/2003 | Brown | |
| 2003/0140106 A1 | 7/2003 | Raguseo | |
| 2003/0163351 A1 | 8/2003 | Brown et al. | |
| 2003/0177193 A1 | 9/2003 | Budge et al. | |
| 2003/0207245 A1* | 11/2003 | Parker | 434/350 |
| 2004/0019259 A1 | 1/2004 | Brown et al. | |
| 2004/0019701 A1* | 1/2004 | McGee et al. | 709/250 |
| 2004/0102685 A1 | 5/2004 | Cosentino et al. | |
| 2004/0117207 A1 | 6/2004 | Brown | |
| 2004/0117208 A1 | 6/2004 | Brown | |
| 2004/0117209 A1 | 6/2004 | Brown | |
| 2004/0219500 A1 | 11/2004 | Brown et al. | |
| 2004/0250210 A1 | 12/2004 | Huang et al. | |
| 2005/0027562 A1 | 2/2005 | Brown | |
| 2005/0080652 A1 | 4/2005 | Brown | |
| 2005/0086083 A1 | 4/2005 | Brown | |
| 2005/0172021 A1 | 8/2005 | Brown | |
| 2005/0172022 A1 | 8/2005 | Brown | |
| 2005/0228883 A1 | 10/2005 | Brown | |
| 2005/0235060 A1 | 10/2005 | Brown | |
| 2005/0273509 A1 | 12/2005 | Brown | |
| 2006/0004611 A1 | 1/2006 | Brown | |
| 2006/0015017 A1 | 1/2006 | Cosentino et al. | |
| 2006/0080152 A1 | 4/2006 | Brown | |
| 2006/0089969 A1 | 4/2006 | Brown et al. | |
| 2006/0100910 A1 | 5/2006 | Brown | |
| 2008/0068447 A1* | 3/2008 | Mattila et al. | 348/14.08 |

FOREIGN PATENT DOCUMENTS

| | | |
|---|---|---|
| WO | 0075748 A2 | 12/2000 |
| WO | 0203284 A1 | 1/2002 |
| WO | 0225551 A1 | 3/2002 |
| WO | 02061526 A2 | 8/2002 |
| WO | 2004038978 A2 | 5/2004 |
| WO | 2006092810 A2 | 9/2006 |

OTHER PUBLICATIONS

PalTalk Instructions http://www.ohiopatient.net/join/paltalk_instructions.htm.

Patient Information Forum http://www.bbc.co.uk/dna/actionnetwork/A13707074.

\* cited by examiner

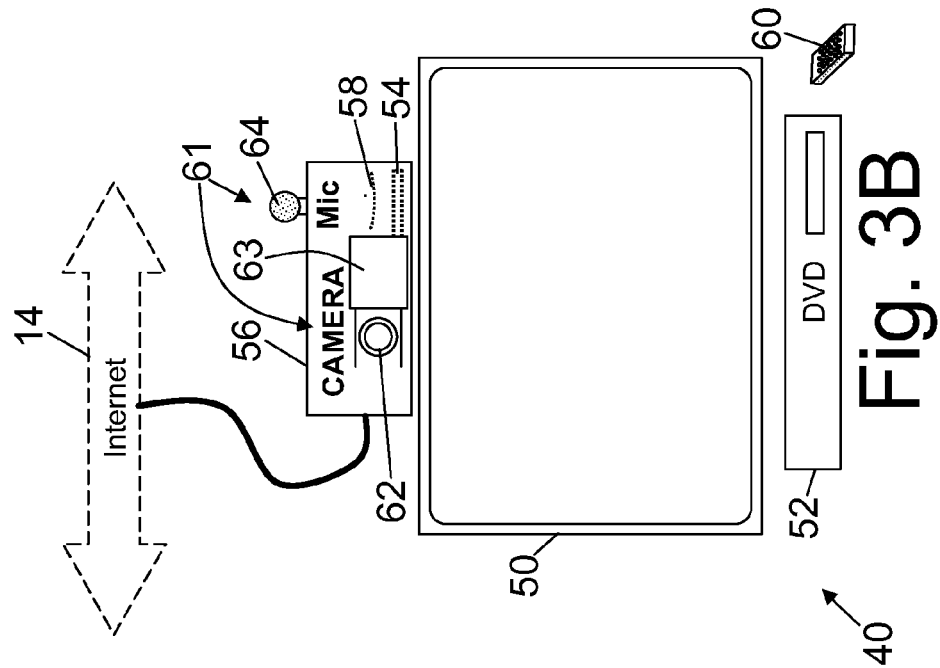
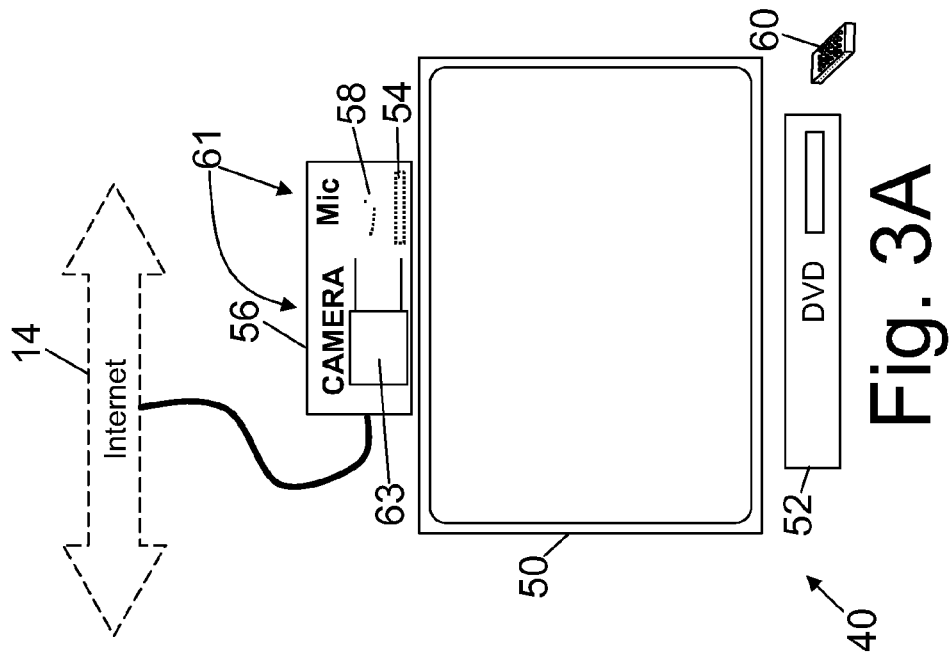

As part of your Care Plan, you have been scheduled to view or participate in the following medical forum:

HIV management    Thursday, Dec. 2, 2009 at 9:00-10:00 a.m.

By participating in this forum, information about your medical condition may be revealed. Therefore, under the provisions of the Health Insurance Portability and Accountability Act (HIPAA) Privacy Rule, your express authorization is required before you may participate in this forum.

Do you authorize your participation in this forum?
- Press (1) for Yes, or (2) for No.

If you elect not to participate in this forum, you may still view the forum. Viewing the forum without participating does not reveal your identity.

Fig. 5

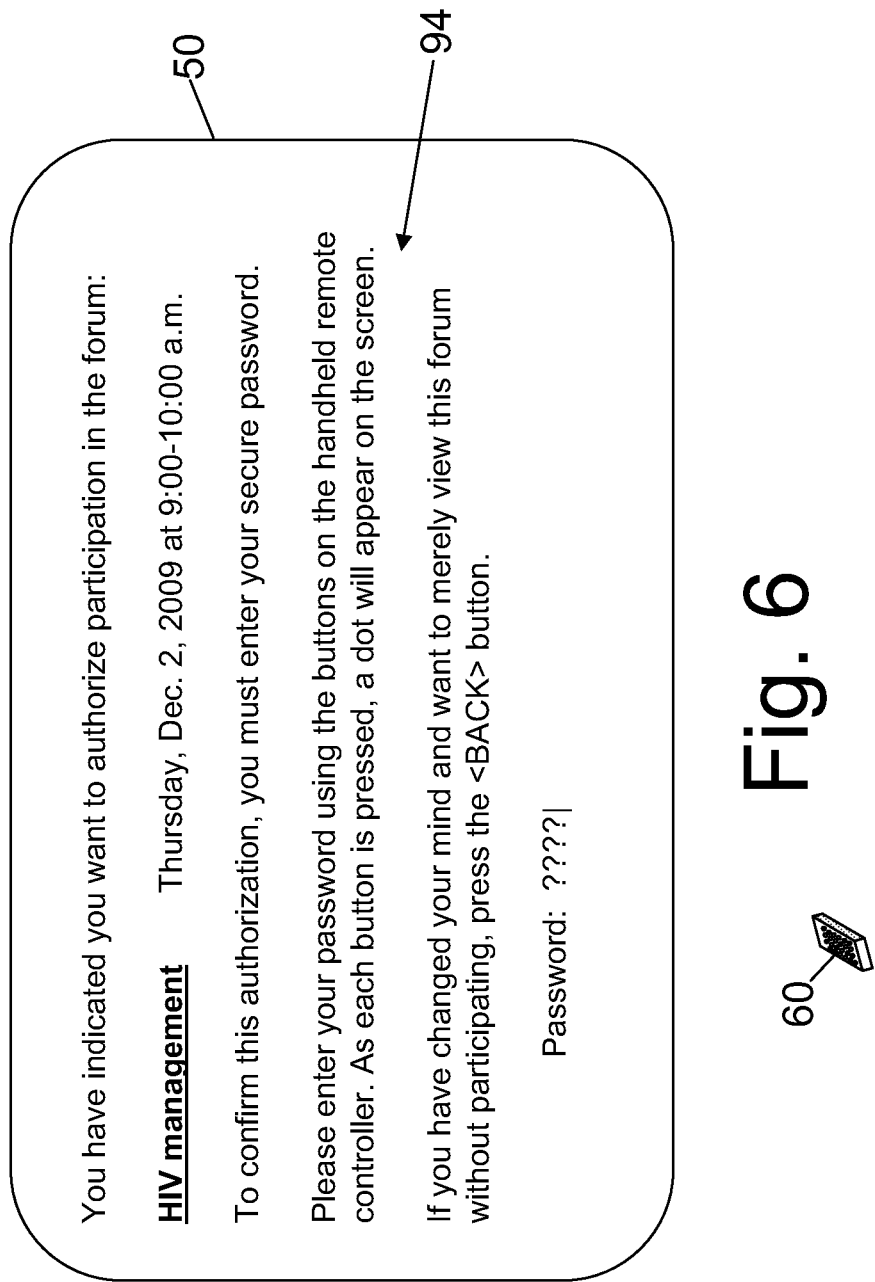
Fig. 6

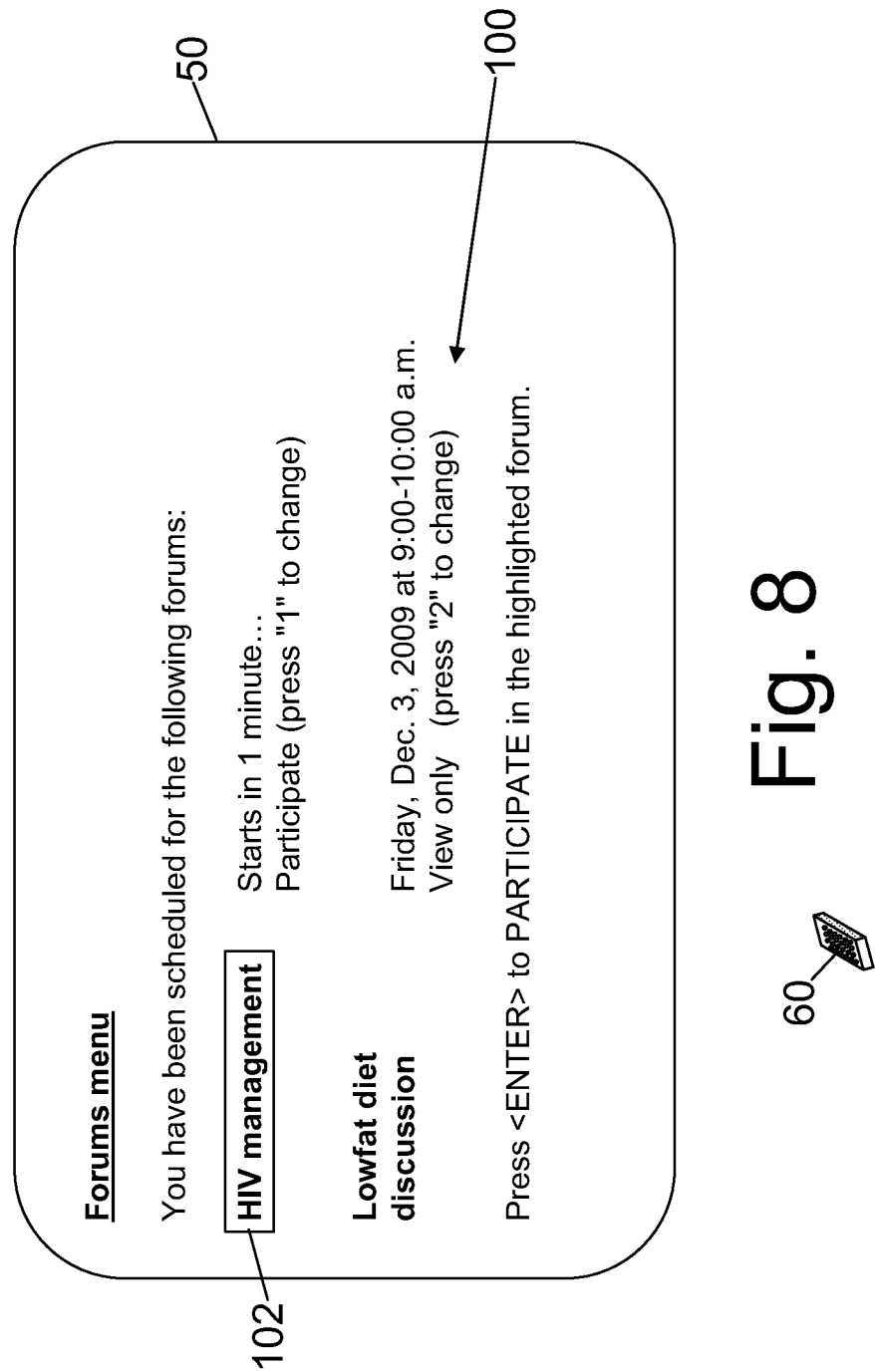
Fig. 8

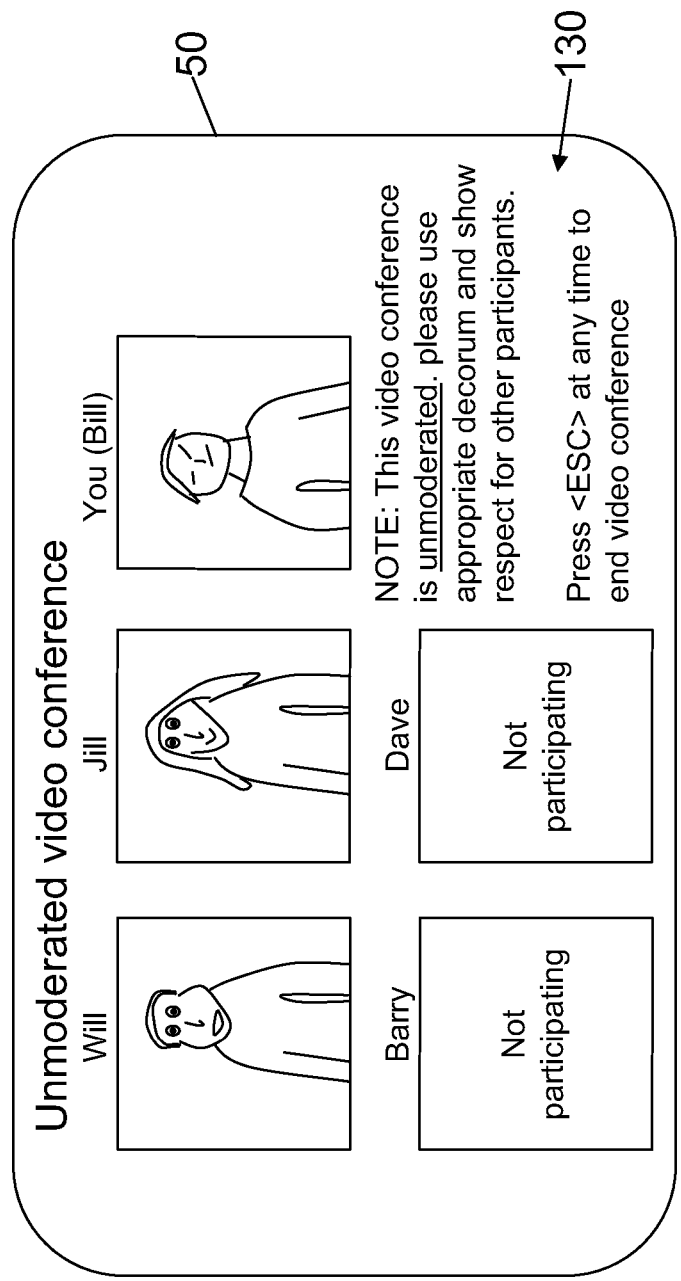
Fig. 13

INTERACTIVE PATIENT FORUMS

The following relates to the medical arts. It finds application in treatment, care, monitoring, and so forth of patients in homes, apartments, nursing care facilities, hospices, hospitals, treatment centers, and so forth.

Chronic illness, deteriorating health conditions, and other medical conditions include both physical and psychological components. The medical care system in the developed world is relatively adept at providing treatment for physical aspects of medical conditions. For example, most hospitals, doctors, medical facilities and so forth provide ready access to advanced surgical facilities, state-of-the-art diagnostic equipment such as MRI, PET, and CT, a plethora of pharmaceuticals for treating a wide range of conditions, excellent physical therapy facilities and trained therapists, dietary programs and dieticians, and so forth.

However, the medical care system can be less adept at recognizing, much less treating, psychological components of illness. Studies consistently show that psychological aspects have a substantial impact upon, and are sometimes even determine of, medical outcomes. Adverse psychological conditions can include depression, loneliness, despair, and so forth. Contrariwise, positive psychological conditions such as a positive mental attitude, social engagement, and hope can enhance the likelihood of a positive medical outcome.

Unfortunately, medical personnel are often poorly positioned to affect these psychological aspects. Effective psychological treatment typically requires ongoing and frequent positive reinforcement, which is difficult for busy medical personnel to provide. Moreover, there are often substantial communication gaps between patients and their physicians or other medical personnel. For example, many chronically ill patients are elderly, while many practicing physicians are substantially younger and have difficulty relating to their elderly patients. Moreover, the mere fact that the patient is suffering the illness while the physician is in most cases generally healthy imposes a substantial barrier to effective understanding.

It has been recognized that the best-positioned persons for providing beneficial encouragement and social interaction with a person with a medical condition is other persons having the same condition or a similar medical condition. This recognition is the genesis of organizations such as Alcoholics Anonymous and other self-help groups. At a minimum, members of such self-help groups have commonality of medical condition, and for a reasonably large self-help group most members are able to locate other members of similar age and other commonalities that facilitate effective social interaction. Chronically ill persons who are unable to maintain steady employment are also more likely to have free time to provide encouragement and support for others.

Heretofore, however, social interaction between persons with the same or similar medical conditions has been hindered by numerous barriers. Some such medical conditions limit mobility, and in extreme cases may cause its sufferers to be housebound or even bedridden. Where mobility is limited, the ability to join and engage in a self-help group is also severely limited.

Medical privacy concerns also inhibit formation of self-help groups in some cases. A doctor may have numerous patients with the same medical condition, but that doctor is generally prohibited from introducing these patients to one another by ethical and legal constraints, since such introductions necessarily would involve impermissible medical disclosures. For example, a doctor cannot tell an HIV-positive patient which others of his or her patients are also HIV-positive, in the hope of starting an HIV support group. Similarly, using patient medical records to identify potential members of a medical self-help group would violate patient-doctor confidentiality, and would also likely violate medical privacy laws such as the Health Insurance Portability and Accountability Act (HIPAA).

It has further been recognized that patient mobility limitations can in principle be overcome using modern communication technologies such as video conferencing. However, putting such concepts into practice has been difficult, for various reasons. Suitable intercommunicating devices are presently not sufficiently ubiquitous in home and other non-medical and non-commercial settings to set up substantial self-help forums. Specialized devices can in principle be provided; however, this introduces substantial cost and can be problematic in view of the "technophobic" nature of many patients. Many patients, for example, are suspicious of new technologies and will resist introduction and use of new technologies in their home or residence. Such a patient may be concerned, for example, that a camera will be used to record their private activities.

The following provides new and improved apparatuses and methods which overcome the above-referenced problems and others.

In accordance with one aspect, a medical communication method is disclosed, which community members have a video conference enabling unit connected with a consumer electronics device disposed in the member's residence. The medical communication method includes identifying two or more of the community members having a selected medical condition or characteristic, and conducting a video conference on a medically related topic between at least two of the two or more identified community members using their respective consumer electronics devices and video conference enabling units.

In accordance with another aspect, a medical forum is disclosed. Audio/video interfaces are disposed in residences of subjects. Each audio/video interface includes a consumer electronics device providing audio/video playback capability and a recording device providing audio/video recording capability. A distributed medical server includes a processor disposed in each residence and operatively coupled with the audio/video interface of that residence. The distributed medical server is configured to perform a video conferencing process via a network including: receiving assent or rejection from a subject regarding joining a selected video conference; and, conditional upon receiving assent from the subject, providing the subject a participatory connection with the selected video conference by which the subject can view the video conference using the playback capability of the consumer electronics device disposed in the subject's residence and can participate in the video conference by being recorded using the recording device disposed in the subject's residence.

In accordance with another aspect, a medical communication system is disclosed. Audio/video interfaces are disposed in residences of subjects. Each audio/video interface includes a consumer electronics device providing audio/video playback capability, and a camera providing audio/video recording capability. A distributed medical server includes a processor disposed in each residence and operatively coupled with the audio/video interface of that residence. The distributed medical server is configured to: (i) play selected portions of pre-recorded audio/video content on the audio/video interfaces of selected residences in accordance with care plan schedules for subjects residing in those residences, and (ii) perform video conferencing in conjunction with selected processors and the Internet in which selected subjects view the video conference using the playback capability of the consumer electronics device disposed in the subject's residence and participate in the video conference by being recorded using the camera disposed in the subject's residence.

In accordance with another aspect, a medical communication method is disclosed, comprising: pushing audio/video content to persons having a selected medical condition or characteristic via a video conference enabling unit connected with a consumer electronics device disposed in each person's residence, the pushing being in accordance with a schedule of a care plan for treating or managing the selected medical condition or characteristic; and moderating a video conference on a topic related to the care plan, the video conference including as participants at least two of the persons having the selected medical condition or characteristic, the video conference being conducted using the participants' respective consumer electronics devices and video conference enabling units and being moderated using at least some equipment that is also used in the pushing of audio/video content.

One advantage resides in facilitating intercommunication amongst persons receiving medical monitoring or intervention.

Another advantage resides in providing psychological support for persons receiving medical monitoring or intervention.

Another advantage resides in facilitating intercommunication amongst persons having a common medical condition while adhering to privacy requisites.

Another advantage resides in providing a person receiving medical monitoring or intervention with a mixture of pre-recorded audio/video content and interactive audio/video content.

Still further advantages of the present invention will be appreciated to those of ordinary skill in the art upon reading and understand the following detailed description.

FIG. 1 diagrammatically shows an illustrative medical communication system.

Figure 2:
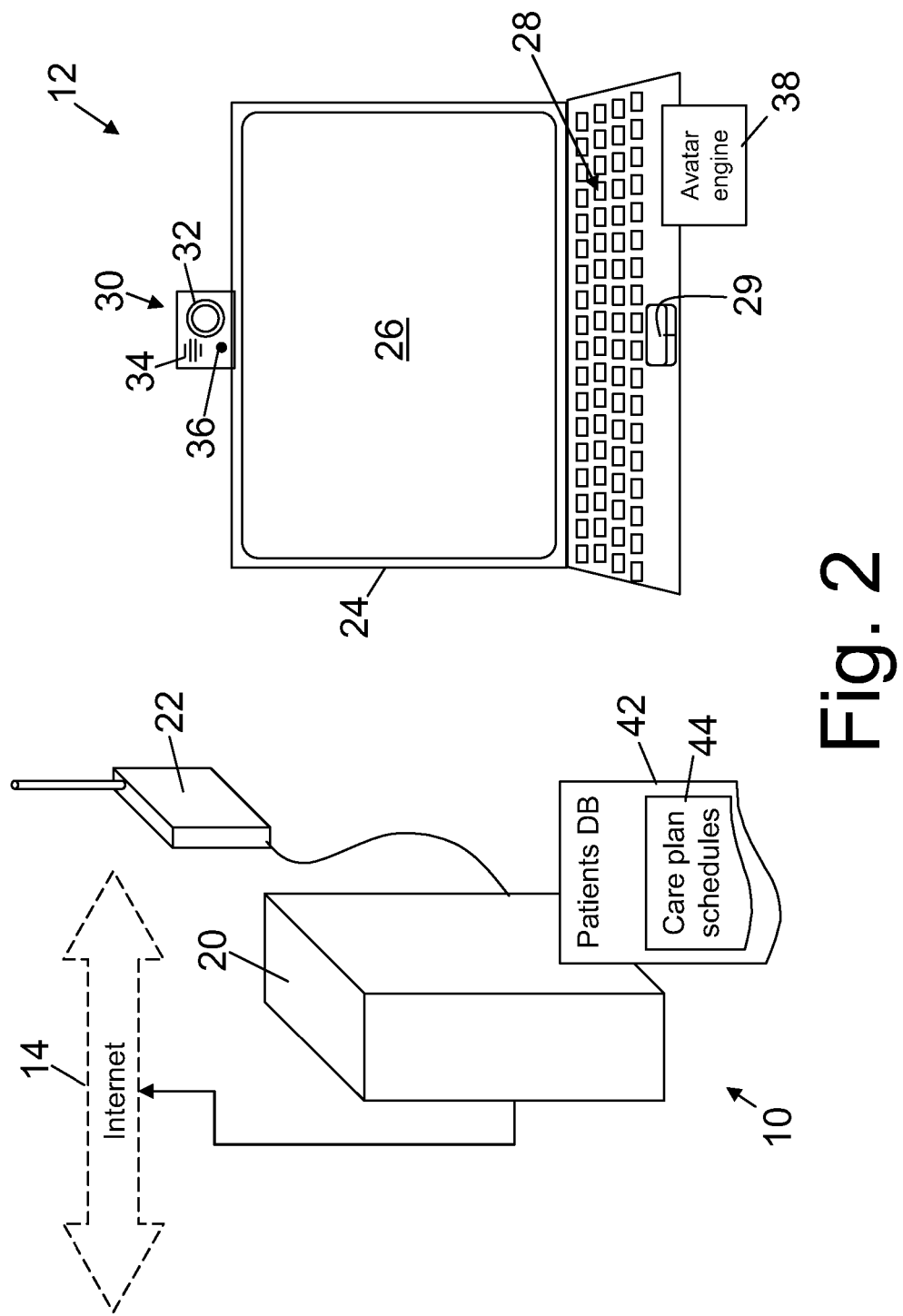

FIG. 2 diagrammatically shows an illustrative embodiment of the medical server of the illustrative medical communication system of FIG. 1.

FIGS. 3A and 3B diagrammatically shows an illustrative embodiment of one of the end-user audio/video recording and playback devices of the illustrative medical communication system of FIG. 1. More particularly:

FIG. 3A shows the illustrative end-user device when it is not recording audio/video content; and FIG. 3B shows the illustrative end-user device when it is recording audio/video content.

Figure 4:
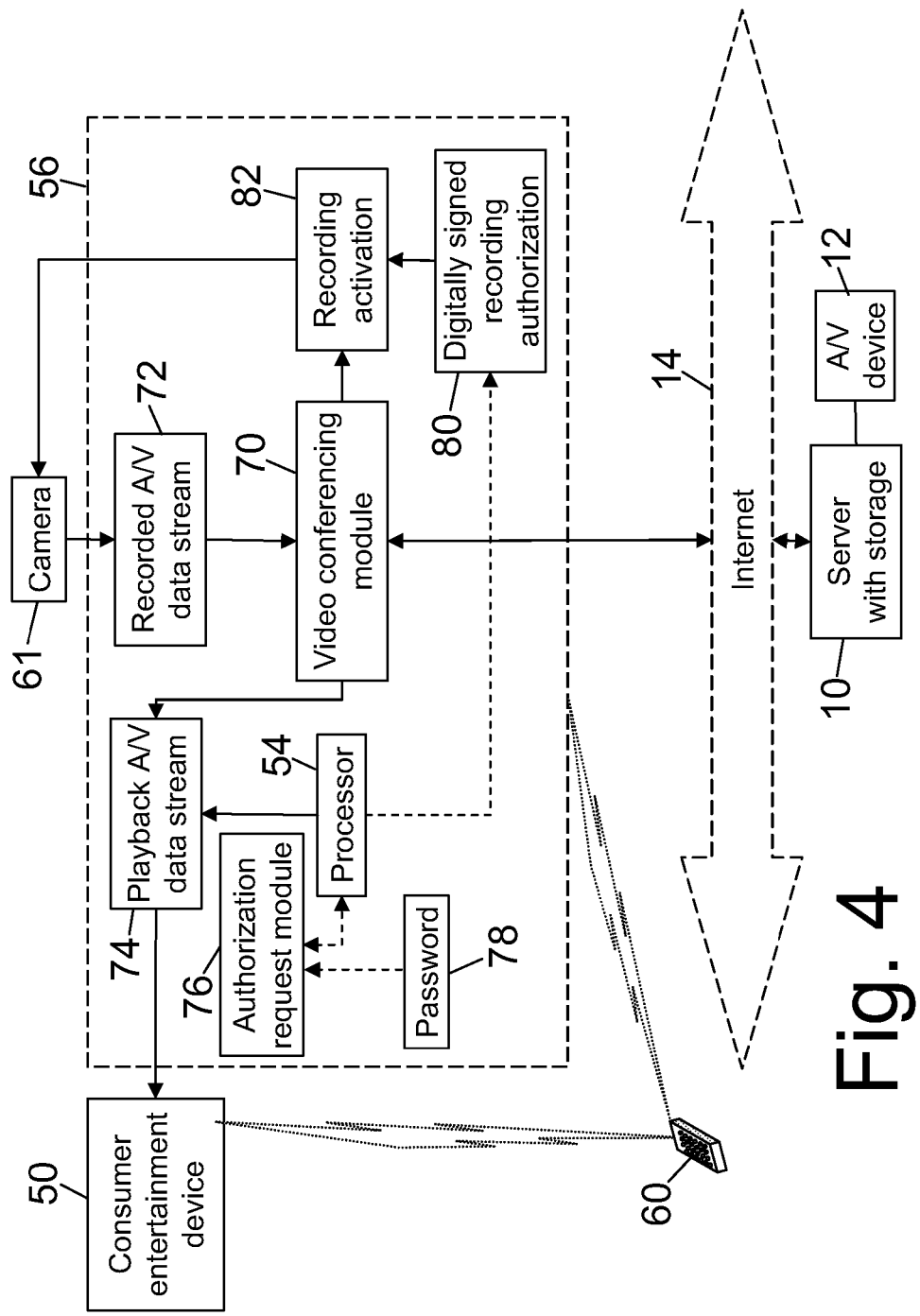

FIG. 4 diagrammatically shows details of the set-top box of FIGS. 3A and 3B that perform video conferencing with authenticated assent.

FIGS. 5-12 diagrammatically show screenshots of a moderated video conference.

Figure 14:
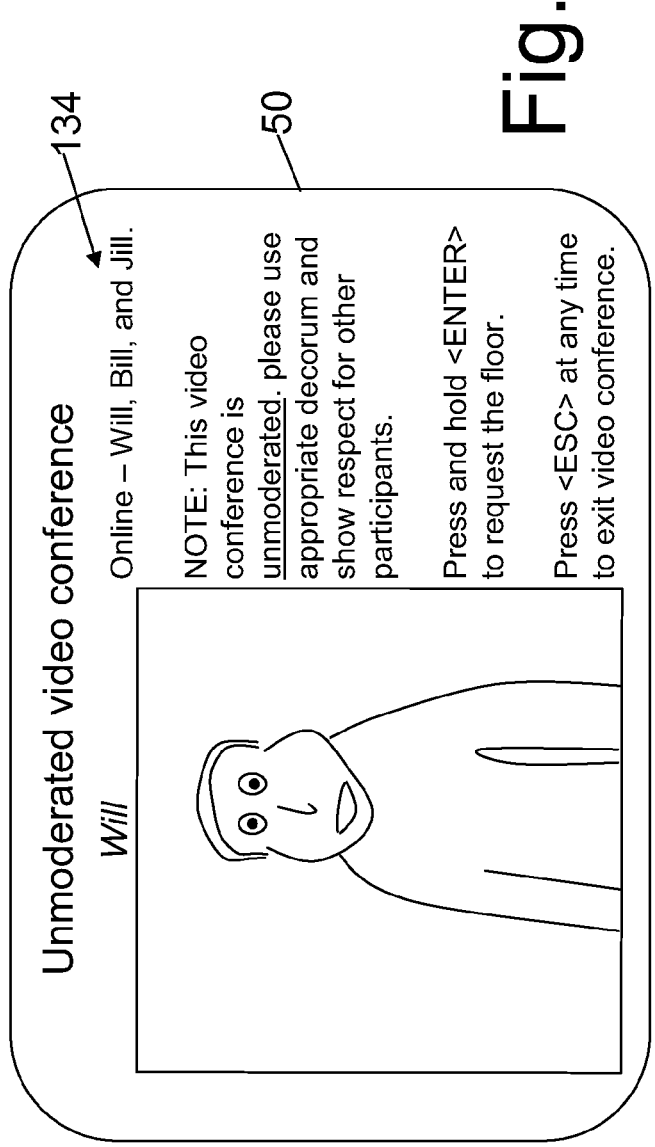

FIGS. 13 and 14 diagrammatically show screenshot of two different unmoderated video conferences.

Figure 15:
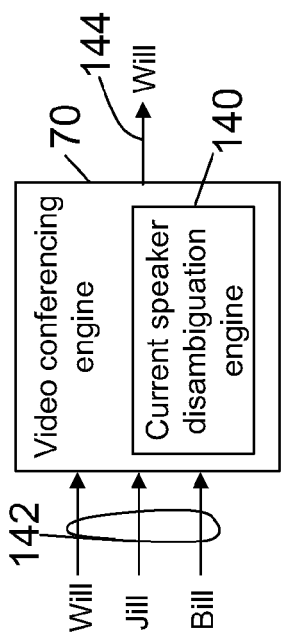

FIG. 15 diagrammatically shows a current speaker disambiguation engine suitable for use in the unmoderated video conference of FIG. 14.

Figure 16:
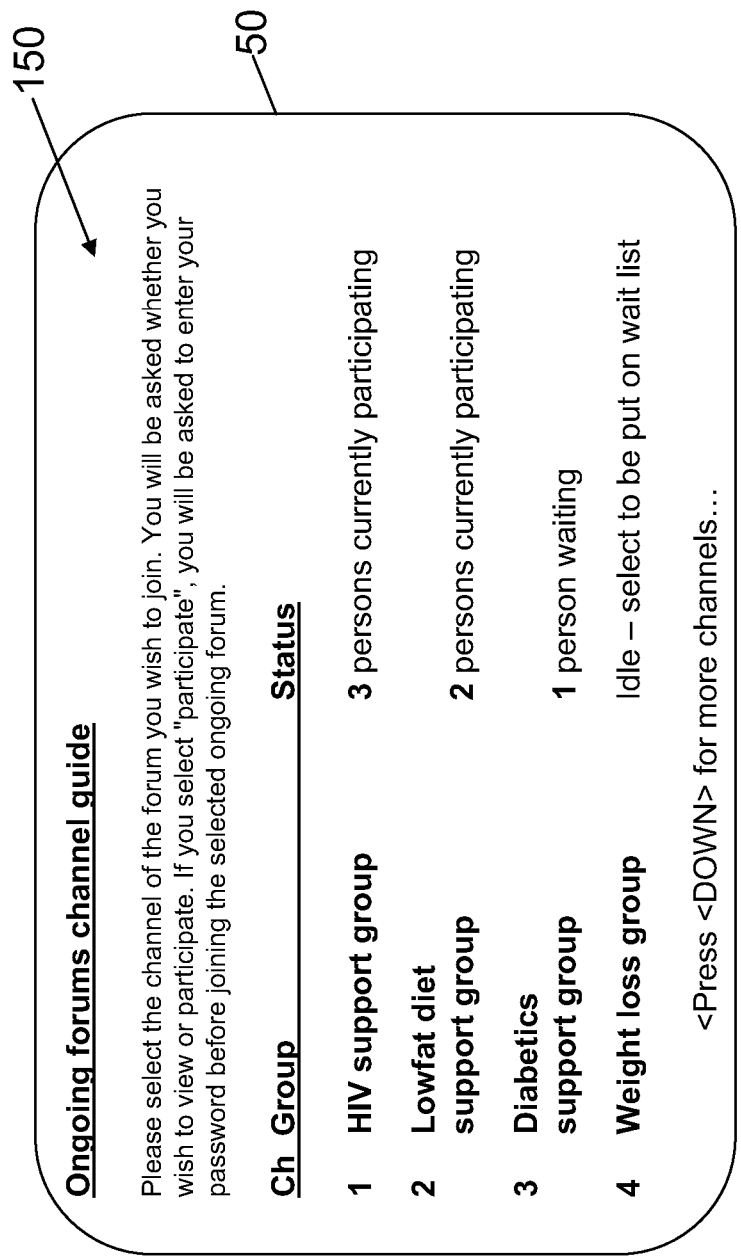

FIG. 16 diagrammatically shows a menu-based interface display for selectively participating in ongoing video conferences in an ad hoc manner.

With reference to FIG. 1, a medical communication system includes a medical server 10 having storage and including an audio/video recording and playback device 12. The medical server 10 is operatively connected with the Internet 14 to send and receive data in an addressed manner. For example, at an Internet Protocol/Transmission Control Protocol (IP/TCP) level, the medical server is addressed using its Internet Protocol (IP) address, diagrammatically indicated as "IP #S" in FIG. 1. At the hypertext transfer protocol level (http, i.e., the world wide web level), the server can be suitably identified by a uniform resource locator (URL) such as, for example, "http://www.medserver.com/", which is converted to an IP address using a Domain Name System or Service or Server (DNS) lookup. In some embodiments, the IP address changes dynamically, and a URL and suitably updated DNS provides the conversion to IP address. While the illustrated embodiment uses the Internet 14 for intercommunication, it is also contemplated to use another network, such as an Ethernet or wireless Ethernet. For Ethernet-based communication, a Media Access Control (MAC) address is suitably used. The communication pathway may include multiple communication media, such as the Internet 14 with an Ethernet link at the server end in the illustrated embodiment.

With reference to FIG. 2, an illustrative medical server 10 includes a central processing unit (CPU) 20 that contains or accesses storage and supports a wireless local area network (WLAN or WiFi, for example), a wired network such as a wired Ethernet, or some combination of wired and wireless local networking. In the illustrative embodiment of FIG. 2, a WLAN is accessed at wireless access points such as an illustrated wireless access point 22 by suitable digital devices such as an illustrated notebook computer 24, or a desktop computer, or a dumb terminal, or so forth. The accessing digital device provides a display 26 for displaying video and one or more input devices such as an illustrated keyboard 28 and touchpad 29. Medical personnel use the notebook computer 24 or other accessing devices to communicate with the medical server 10. Such medical personnel may include, for example, nurse assistants, nurses, doctors, medical administrative personnel, care plan providers, designers, and coordinators, support or contract workers for a medical or medically related organization, or so forth.

In the illustrated embodiment, the accessing digital device also defines the audio/video recording and playback device 12. The notebook computer 24 includes the display 26 to provide video playback, and typically also includes built-in speakers to provide audio playback. Alternatively or additionally, external speakers (not shown) may be connected with the computer. For recording, an illustrated camera 30 includes a video recording lens 32 and a microphone 34. An indicator light 36 or other indicator optionally activates during recording. In various embodiments, the camera may be integrated into the computer, or may be embodied as a standalone camcorder or so forth. In some embodiments, it may be undesired to have the medical person be video-recorded. In such a circumstance, the video of the medical person can be replaced by a suitable animated virtual avatar simulating a medical professional implemented by a suitable avatar engine 38. (The avatar engine 38 is illustrated diagrammatically, and may for example be physically embodied as software executing on the notebook computer 24, software executing on the server CPU 20, or so forth).

With reference to FIG. 1, the medical server 10 is intended to service a substantial number of chronically ill patients, elderly patients, ill persons, or other end-users. As used herein, the term "patient" is to be broadly construed as encompassing conventional patients in hospitals as well as out-patients, chronically ill persons under continuing out-patient-type medical care for a chronic condition, elderly or frail persons under ongoing medical surveillance through scheduled visits to the doctor's office, persons seeking assistance with a physical or mental condition, or so forth. In one approach, the serviced persons are members of a virtual community that is serviced by the medical server 10. The community members may include, for example, patients of a medical facility, outpatients of a hospital system, nursing home residents, retirees, or so forth who sign up for or otherwise agree to join the virtual medical community. Such a virtual community may be open to anyone who wants to join, or may be restricted to a certain class of members, such as retirees of a sponsoring corporation or patients of a selected medical institution or medical system. The virtual community is a distributed community in which the community members reside in their own homes, or in nursing home residences, or so forth. Each community member has an end-user audio/video recording and playback device 40 operatively connected with the medical server 10 via the Internet 14. Such access is addressed, for example using the IP addresses of the end-user audio/video recording and playback devices 40 as illustrated, so that communication from the medical server 10 can be targeted to specific end-user audio/video recording and playback devices 40. While four end-user audio/video recording and playback devices 40 are illustrated in FIG. 1 as examples, typically the number of end-user audio/video recording and playback devices may number in the dozens, hundreds, or more. Typically, the end-user audio/video recording and playback device 40 are located in the residences (e.g., homes, apartments, nursing home rooms, hospice rooms, retirement community rooms, or so forth) of the associated end-users.

With reference to FIG. 2, to accommodate this substantial number of end-users, a patients database 42 is maintained at the medical server 10. The patients database 42 typically includes address information, such as the illustrated IP addresses, for each end-user audio/video recording and playback device 40. In some embodiments, the patients database 42 further includes care plan schedules 44 that schedule audio/video content or other information to target to each end-user. Thus, for example, an end-user having heart problems may be scheduled for cardiac therapy videos, diet videos, or so forth, while an end-user suffering from diabetes may be scheduled for insulin injection instructional videos, low-salt diet videos, and so forth.

FIG. 2 diagrammatically illustrates the example medical server 10. More generally, the medical server can be embodied by various combinations of hardware and software. For example, in some embodiments a single computer may both host the server and provide user interfacing including embodying the audio/video recording and playback device. In other embodiments, the server may be embodied by a cluster or network of computers, or so forth. Although the single interfacing notebook computer 24 is illustrated as an example, it is contemplated for numerous medical personnel, possibly numbering in the tens, hundreds, or more, to access the medical server 10 via one, two, a few, a few dozen, a few hundred, or more computers or other interfacing digital devices. In some embodiments, some such interfacing computers or digital devices may omit the audio/video recording and playback device, or may omit the recording capability.

With continuing reference to FIG. 1 and with further reference to FIGS. 3A and 3B, an illustrated end-user audio/video recording and playback device 40 is diagrammatically shown as an example. The end-user audio/video recording and playback device 40 differs from the audio-video recording and playback device 12 of the medical server 10 in certain ways that reflect substantial differences between the typical end-user as compared with the typical medical person. End-users tend to be older, more frail (i.e., less healthy), and, as a group, less technically sophisticated than medical personnel. For example, some end-users may be uncomfortable with a computer, or may be unable to operate a computer due to physical or mental limitations. To alleviate these concerns, the illustrated end-user audio/video recording and playback device 40 is built around a consumer entertainment device, such as an illustrated television 50 and DVD player 52. The television 50 may be a standard definition television or a high-definition television, may employ a cathode-ray tube display, LCD display, plasma display, or so forth, and may include built-in audio speakers or be connected with external speakers or an external sound system such as a surround-sound system. The DVD player 52 is optionally omitted, or replaced or supplemented by a video cassette recorder (VCR), a DVD recording device, a digital video recorder (DVR), or so forth. The consumer entertainment device optionally includes other components such as, for example, a gaming machine, cable television box, satellite dish, or so forth.

The end-user audio/video recording and playback device 40 further includes a processor 54 that facilitates interfacing with the medical server 10 via the Internet 14. The illustrated processor 54 is housed in a designated housing such as an illustrated set-top box 56 or other unit, and hence the processor 54 is shown in phantom. In other embodiments the processor may be integrated into the television 50, or integrated into a cable box (arrangement not shown), or so forth. The illustrated set-top box 56 also houses a data storage 58, such as an illustrated hard drive again shown in phantom since it is enclosed in the set-top box 56. In other embodiments, the data storage may include a solid state electronic storage medium such as a flash memory, an optical medium such as a recordable optical drive, or so forth.

As is known in the art, consumer entertainment devices such as the illustrative television 50 and DVD player 52 are commonly controlled by one or more hand-held remote controllers. In the illustrated embodiment, a common hand-held remote controller 60 is effective to operate the television 50, the DVD player 52, and the set-top box 56. The hand-held remote controller 60 may be a commercial universal-type remote controller, for example, that is readily configured to control the multiple devices 50, 52, 56. In other embodiments, the hand-held remote controller 60 may be a specially constructed remote controller that, for example, includes extra-large buttons, simplified controls, or so forth, to facilitate ease-of-use by the end-user who may be ill, infirm, or otherwise impaired. Although the illustrated hand-held remote controller 60 is a universal-type remote controller that enables control of all the devices 50, 52, 56, it is also contemplated to have a hand-held remote controller for operating the set-top box 56 that is separate and distinct from one or more other hand-held remote controllers for controlling the consumer entertainment devices 50, 52.

In some embodiments the end-user audio/video recording and playback device 40 is located in the end-user's home, for example in the living room or bedroom. Some end-users may therefore be concerned about personal privacy and security, especially in view of the audio/video recording capability of the end-user audio/video recording and playback device 40. To alleviate these concerns, the recording components are optionally configured to reassure the end-user that recording is not performed surreptitiously or without the end-user's knowledge and control. In the illustrated end-user audio/video recording and playback device 40, a camera or other audio/video recording device 61 includes a video recording lens 62 having an automatic lens cover 63 arranged to physically block the video recording lens 62 (as shown in FIG. 3A) except during recording of audio/video content (as shown in FIG. 3B, where the automatic lens cover 63 is automatically moved away to reveal the video recording lens 62). That is, the automatic lens cover 63 is programmed or otherwise interlocked to be open whenever video is being recorded, and to be closed otherwise. By physically blocking the video recording lens 62 from view when it is not in use, the end-user is reassured of his or her privacy. Similarly, the camera 61 further includes a microphone 64 is configured to extend at least partially out of the set-top housing during recording (as shown in FIG. 3B) and retracts into the housing otherwise (as shown in FIG. 3A). While such retraction does not in fact prevent recording, the hiding of the microphone 64 when not in use may nonetheless be reassuring to the end-user.

FIGS. 3A and 3B diagrammatically illustrate the example end-user audio/video recording devices 40. For example, the illustrated embodiment advantageously makes use of the existing television 50. However, it is also contemplated to replace the television by a dedicated replacement consumer entertainment device that integrates the processor, hard drive, and optionally other components into a single housing. While the illustrated camera 61 advantageously reassures the end-user of his or her privacy and security, in other embodiments a camera without such privacy reassurances or with less aggressive privacy reassurances is contemplated, such as a camera that uses an LED recording indicator rather than the lens-blocking automatic lens cover 63. On the other hand, it will be appreciated that the automatic lens cover 63 and the retractable microphone 64 will find broader application that is not limited to the disclosed medical communication systems. For example, the automatic lens cover 63 can be usefully employed in any situation where it is advantageous to assure the subject of privacy and security, and may for example be used in cameras for studios that record children, in cameras used for photographing drivers for use on drivers' licenses, and so forth.

It is to be appreciated that the illustrated medical communication system can also be viewed as a distributed medical server including the processors 58 and the medical server 10, which interacts with the audio/video interfaces that include the end-user audio/video recording and playback devices 40 and the cameras 62, 64. The distribution of processing capability of the distributed medical server can vary; for example, the pre-recorded audio/video content, or relevant portions thereof, can be stored on the set-top boxes 56 and recalled at the instigation of the medical server 10, or can be stored at the medical server 10 and streamed to the targeted set-top box 56, or so forth.

Typically, the medical communication system is used to push content from the medical server 10 to targeted end users. Toward this end, based on the care plan schedules 44 the medical server 10 conveys pre-recorded audio/video content targeted to a particular end-user by transmitting the pre-recorded audio/video content to the end-user audio/video recording and playback device 40. For example, in IP/TCP such targeting is suitably achieved by transmitting the pre-recorded audio/video content to the end-user audio/video recording and playback device 40 using the IP address of the device 40 for targeted addressing. Alternatively, the pre-recorded content may be stored on the set-top box 56 of the targeted end-user, and the medical server 10 conveys an identification of the portion of such pre-recorded content to be presented.

The pre-recorded audio/video content that is transmitted or identified is selected based on the care plan schedule 44 to relate to health concerns, issues, wellness, or the like pertaining to the targeted end-user. For example, if the end-user has heart problems, the pre-recorded audio/video content may include exercise videos, diet lessons, instructions on taking medications, or so forth. The pre-recorded audio/video content may also include encouragement messages. In some embodiments, the pre-recorded audio/video content is interactive in a structured way. For example, the pre-recorded audio/video content may include an interactive survey which the end-user answers by inputting responses using the hand-held remote controller 60, and these structured responses are sent back to the medical server 10 via the Internet 14.

At the end-user audio/video recording and playback device 40, the transmitted pre-recorded audio/video content is stored, for example on the hard disk 58, and played back at the end-user's request. In a suitable approach, the processor 54 provides a graphical user interface in cooperation with the television 50 which enables selective playback of pre-recorded audio/video content received from or identified by the medical server 10. For example, the processor 54 may be programmed to receive the pre-recorded audio/video content at night when Internet usage is low, and stores received pre-recorded audio/video content on the hard drive 58. The user then turns on the television 50 and selects the medical graphical user interface using suitable power and select buttons on the hand-held remote controller 60. In response, the processor 54 causes the television 50 to display a menu of textual and optionally graphical items including a list of audio/video offerings including at least the received pre-recorded audio/video content.

The pre-recorded audio/video content is principally one-way (i.e., server-to-end user), with optional structured responses such as survey responses optionally communicated from the end-user back to the medical server 10. This approach is good for conveying medical information to the end-user. However, it is a relatively passive mechanism from the end-user's standpoint, and does not provide the end-user with full psychologically beneficial human interaction. The pre-recorded content advantageously provides the end-user with some feedback and encouragement; however, still more effective psychological or emotional support is advantageous.

With reference to FIG. 4, toward this end the set-top box 56 is configured to perform a video conferencing process via the Internet 14. In the illustrated embodiment, a video conferencing module 70 is configured to receive a recorded audio/video data stream 72 generated by the camera 61, so as to enable the end-user to participate in a video conference by being recorded using the camera 61 disposed in the subject's residence. The video conferencing module 70 optionally performs digital signal processing of the recorded audio/video data stream 72 such as data compression, image stabilization, echo cancellation, or so forth, and communicates the recorded and processed audio/video data stream to other participants or viewers via the Internet 14. Such recording is in some embodiments performed continuously, while in other embodiments recording is only performed at selected times such as when the end-user is speaking or when the end-user presses a button on the handheld remote controller 60 to initiate recording. As will be discussed, in some embodiments the end-user optionally does not participate in the video conference but instead merely watches or views the video conference—in such cases, the available recording functionality is not used. Optionally, the non-participating end-user may have the option of providing limited contributions to the video conference in a manner not likely to compromise anonymity, such as by providing text input or audio input (the latter optionally filtered to reduce likelihood of voice identification). The video conferencing module 70 also receives from the Internet 14 audio/video content showing other participants, an optional moderator, selected graphics, or other audio/video content of the video conference. The video conferencing module 70 optionally performs digital signal processing on this received content, such as data decompression, format conversion, or so forth, and generates a playback audio/video data stream 74 that is played back on the television or other consumer entertainment device 50. The video conferencing module 70 may be embodied wholly as software executing on the processor 54 (possibly in conjunction with data swapping or other interaction with the hard disk 56) or may be embodied as a combination of hardware and software. For example, the video conferencing module 70 optionally performs data compression and decompression using a codec embodied as software executing on the processor 54, or using a codec embodied as an application-specific integrated circuit (ASIC).

The video conference is suitably controlled by the distributed medical server using a centralized control, such as a multi-point control unit that bridges the signals from two or more end-users. In this centralized approach, the video conferencing modules 70 of the viewing or participating end-users communicate with a common multi-point control unit, for example embodied as software and optional dedicated hardware integrated with or communicating with the medical server 10. In some embodiments, a moderator participates in the video conference via the audio/video recording and playback device 12. Alternatively, one of the participating set-top boxes 56 can be configured as a common multi-point control unit, in which case the medical server 10 is not involved. For example, a conference-initiating end-user can contact other end-users via the IP addresses, URL's or other addresses of other end-users, and the video conferencing module 70 of the set-top box 56 of the conference-initiating end-user configures as the multi-point control unit. Alternatively, decentralized multi-point control may be used, in which there is not multi-point control unit. In this approach, each participating set-top box transmits its audio/video to all other participating and viewing set-top boxes.

The video conference typically relates to medical aspects, such as a medical condition, personal frailty, mental or physical disability or handicap, or so forth. By participating in such a video conference, an end-user potentially loses his or her anonymity and reveals private medical information. For example, an end-user who joins an acquired immune deficiency syndrome (AIDS) support group video conference reveals, by participating, that the end-user likely has AIDS or likely tested positive for the human immunodeficiency virus (HIV) that causes AIDS. Accordingly, there are medical privacy ramifications to participating in the video conference. Such medical privacy ramifications may include, for example, ethical obligations of the video conferencing provider not to reveal private medical information, legal aspects such as the need to comply with the Health Insurance Portability and Accountability Act (HIPAA), or so forth.

In some approaches, these privacy issues are dealt with at the time the end-user joins the medical communication system. For example, the potential medical privacy ramifications may be explained to the end-user at the time he or she receives the set-top box 56, and the end-user may be asked to sign suitable forms granting express assent to joining video conferences in view of these understood medical privacy ramifications.

With continuing reference to FIG. 4, in an alternative illustrated approach the set-top box 56 is optionally configured to obtain the express assent of the end-user before joining each video conference. In the illustrated approach, an authorization request module 76 executes on the processor 54. The authorization request module 76 informs the end-user of potential medical privacy ramifications at the time the end-user attempts to join a selected video conference, and receives assent or rejection from the end-user regarding joining the selected video conference. The authorization request module 76 preferably requires that the end-user enter a password 78 to confirm the end-user's identity when assenting. Optionally, the password 78 is used to create a digitally signed recording authentication 80 that is used to authorize recording activation 82 by the video conferencing module 70.

A difficulty with this authentication approach is that it can lead the end-user to refuse to participate in video conferences that may be of value to the end-user. In other cases, an end-user may not want to participate in particular video conference because the end-user is not sure about that particular video conference. For example, an end-user who has previously participated in video conferences on topics such as weight loss or exercise may nonetheless be uncertain about participating in a video conference pertaining to AIDS support, or relating to prospective heart surgery.

To address these concerns, in some embodiments the effect of rejecting (i.e. refusing assent to) a particular video conference only has the effect of preventing the end-user from participating in the video conference—the end-user can still view the video conference without participating and hence remain anonymous. In this way, the end-user can see the video conference and, if it is of interest and the end-user is willing, the end-user can elect to assent to participating. It is expected that in many cases an end-user who is initially hesitant to participate in a video conference may become willing to do so upon viewing the ongoing video conference and seeing who is participating. Moreover, even if the end-user does not elect to participate, merely viewing the video conference without ever participating may be beneficial. In another embodiment, the set-top box includes an avatar system that permits the potential conferee to modify his or her facial appearance possibly substituting an animated character. A first name name-only or alias policy is also contemplated. Such an anonymity policy could be optional or mandatory. In similar fashion, in some embodiments it may be undesired to have the moderator be video-recorded. In such a circumstance, the video of the moderator can be replaced by a suitable animated virtual avatar implemented by the avatar engine 38.

Having described with reference to FIG. 4 an illustrative medical communication system including video conferencing capability, some example video conference sessions are described.

With reference to FIGS. 5-12, an illustrative moderated video conference (also called a "forum" herein) pertaining to HIV management is described by way of example. FIG. 5 shows a suitable interface by which an end-user is invited to the HIV management video conference. In the illustrated case, the HIV management video conference is scheduled as part of the end-user's care plan schedule. That is, in addition to scheduling the playback of selected pre-recorded audio/video content, the care plan schedule for this particular end-user further includes the HIV management video conference. The invitation may arise in various ways. In some embodiments, the care plan may incorporate such invitations automatically. For example, anyone having a care plan with an HIV management component may be invited to the HIV management video conference. In some embodiments, invitations may be made responsive to certain care plan responses. For example, any patient whose HIV management care plan is not proceeding apace toward the desired outcome may be invited to an HIV management video conference where it is desired that participants will discuss and hopefully overcome their lack of adequate progress. In some embodiments, a given video conference may have a maximum number of allowed members, to ensure that the group size is manageable. In some embodiments, successive video conferences may include the same invitees, so as to develop a repertoire and level of trust amongst the participants over time. In some embodiments, the invitees may share a commonality beyond a shared medical condition or characteristic, such as all participants being patients of the same physician, or all patients being from the same geographical region, or so forth.

The invitation is displayed on the end-user's television 50 under control of the set-top box 56. The invitation informs the end-user of the scheduled HIV management video conference including the day and time. It further provides a statement 90 of the potential medical privacy ramifications, and a request 92 for the end-user to either assent to or reject participation in this forum. The end-user suitably makes the selection using the handheld remote controller 60. The request 92 notes that if the end-user elects not to participate in this forum, the end-user may still view or audit the forum without participating so as to not reveal the end-user's identity. Optionally, a related screen may be presented which requires the user to agree to keep the identities of other participating individuals confidential. In some embodiments, the auditing option may be omitted—for example, if the topic of the video conference is highly sensitive then the participants may not want to have unknown anonymous observers.

Figure 7:
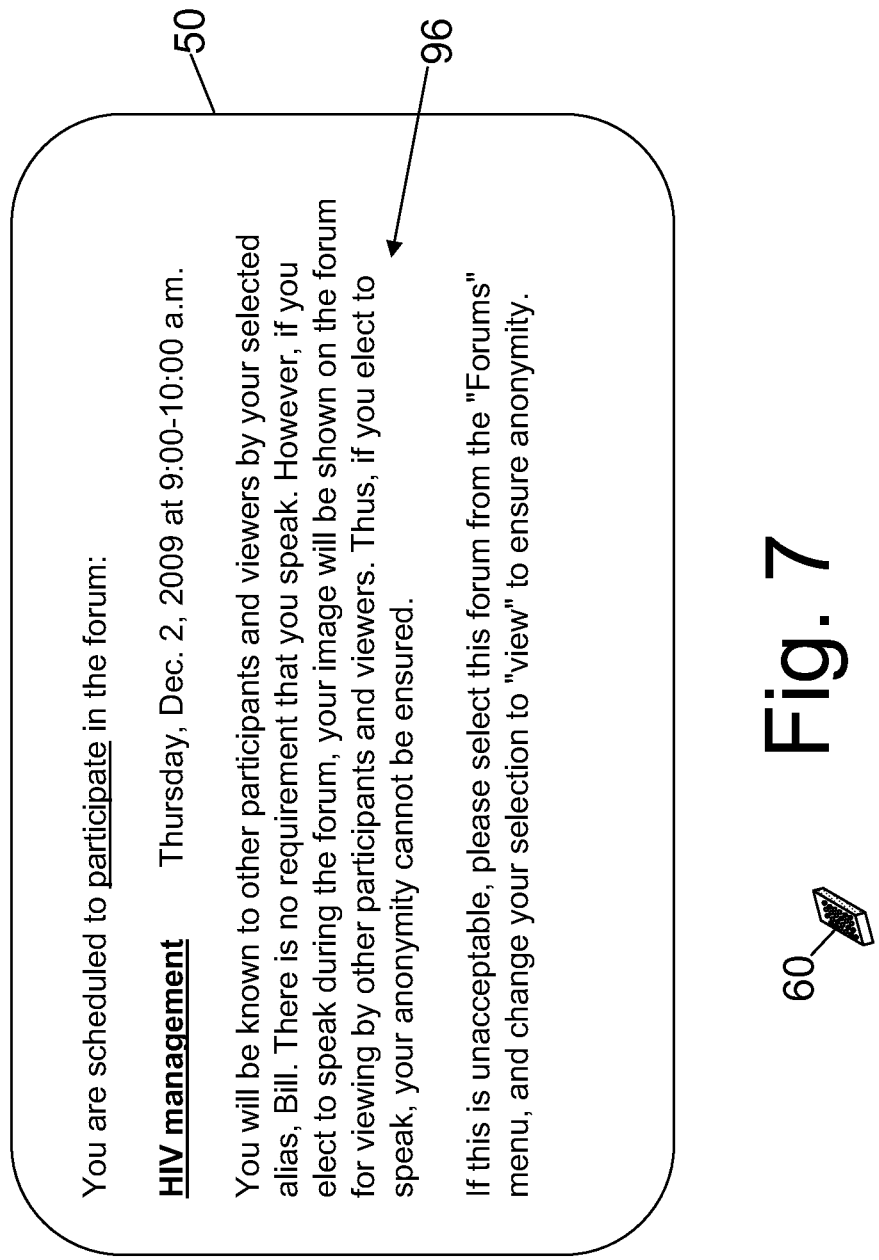

With reference to FIGS. 6 and 7, displays are shown that suitably appear after the user assents via the display of FIG. 5. The display of FIG. 6 includes a password entry dialog 94 that enables the end-user to enter his or her password so as to confirm the assent. Optionally, the entered password is used to generate a digital signature or other record of the authenticated assent. The display of FIG. 7 appears after the password is successfully entered, and confirms that the end-user is scheduled to participate in the HIV management forum. A confirmation dialog 96 informs the end-user that he or she will be known by the end-user's selected alias "Bill". This alias was suitably selected when the end-user joined the medical communication system, or was previously selected or revised via another user interface dialog (not shown). The confirmation dialog 96 re-emphasizes potential medical privacy ramifications, and notes that the end-user optionally may elect not to speak and hence avoid being imaged during the video conference.

The operations depicted in FIGS. 5-7 are suitably performed some time before the scheduled start of the HIV management video conference. For example, these operations may be performed a day, week, month, or longer before the scheduled start of the HIV management video conference.

With reference to FIG. 8, the user interface provided by the distributed server system and displayed on the television 50 suitably includes a user-accessible "Forums menu" 100 that lists the forums the end-user is scheduled to participate or view. In the view shown in FIG. 8, the end-user has highlighted 102 the HIV management forum which at the time depicted in FIG. 8 is scheduled to start in one minute. The end-user suitably presses <ENTER> on the handheld remote controller 60 to join the HIV management forum. As shown in FIG. 8, the end-user is also scheduled to view (but not participate in) a later lowfat diet discussion video conference. The forums menu 100 gives the user the option of changing the status of a scheduled forum. For example, the user can press "2" on the handheld remote controller to change the status of the lowfat diet discussion window, for example to remove that video conference from the schedule listed in the forums menu 100 or to change from "view only" status to "participate" status in a manner analogous to that shown in FIGS. 5-7.

Figure 9:
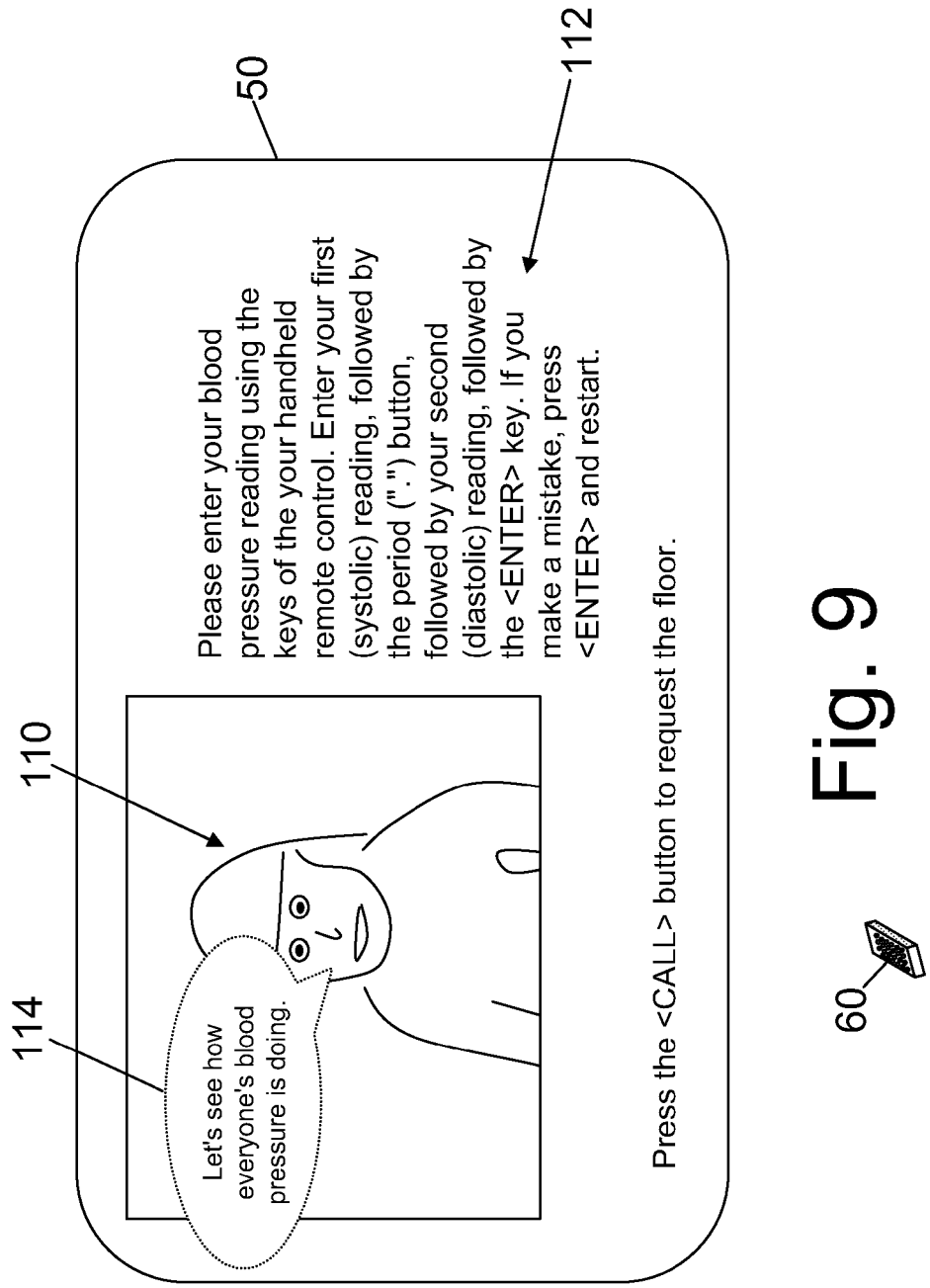

FIG. 9 shows a snapshot of the HIV management video conference once it is in progress. The video content of the video conference appears on the television 50, and at the snapshot shown in FIG. 9 includes an image of a moderator 110, such as a nurse, and associated text 112. The illustrative HIV management video conference of FIGS. 5-12 is a moderated video conference in which at least the video content shown to participants is controlled by the moderator. In some embodiments, the moderator may be one of a group of nurses or other medical professionals or employees who have received suitable training in the operation of the video conference monitoring equipment (e.g., notebook computer 24 running video conferencing monitoring software) and who have received training or are otherwise qualified to moderate a group of participants. The moderator preferably has some knowledge about the medical condition or characteristic shared by the participants of the video conference. In some embodiments, the moderator may be a physician or other medical person who uses the video conference as a forum for managing a group of patients under the medical person's care. For example, the moderator may be a physical therapy specialist who is assigned a group of patients, and that group of patients makes up the invitees to the video conference. The physical therapy specialist uses the video conference at least in part to check up on the patients' progress and to convey advice on how to best implement the assigned physical therapy activities.

At the snapshot shown in FIG. 9, the moderator has selected to display the text 112 asking each participant to enter his or her blood pressure reading. The integrated display of FIG. 9 showing streaming video (the image of the moderator 110) and static text 112 is readily generated by standard image processing techniques; for example, such processing can start with a static image of a background and the text 112 and replace pixels in the image region with the pixels of the streaming video, generating such composite images at the frame repeat rate of 30 frames/per/second or the like. In this illustrative example, each participating end-user has been issued a blood pressure cuff or other blood pressure measurement device for use at the end-user's home or other residence, and the moderator has verbally asked 114 the participants to measure and enter their blood pressure readings. (In FIG. 9 and elsewhere in the FIGURES, audio content of the video conference is diagrammatically indicated using dialog balloons). As instructed in the text 112, each end-user can enter his or her blood pressure reading using buttons of the handheld remote controller 60.

Figure 10:
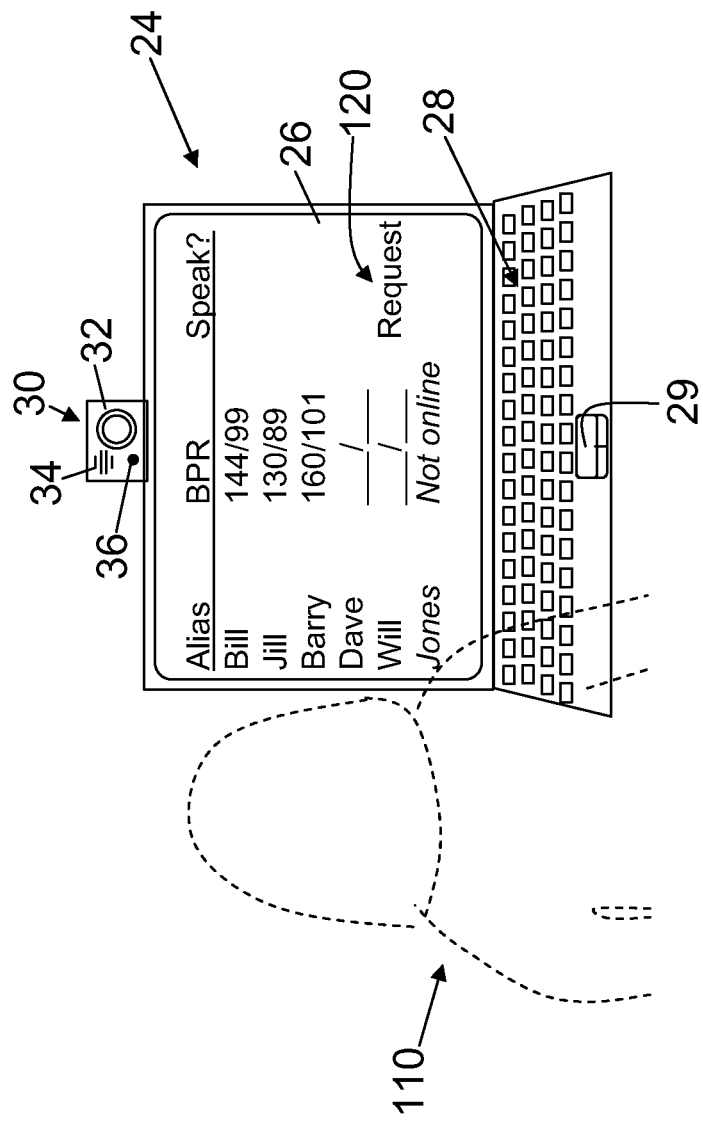

FIG. 10 shows a snapshot of the same point in time in the HIV management video conference as that of FIG. 9, but from the perspective of the moderator 110. In FIG. 10, the moderator 110 is shown in phantom viewing the display 26 of the notebook computer 24 that is being used by the moderator 110 to moderate the HIV management video conference. The display 26 is showing the blood pressure readings as they are entered by the end-users and communicated to the server 10 via the Internet 14 and thence to the notebook computer 24. FIG. 10 shows a list of five participants identified by their aliases: "Bill", "Jill", "Barry", "Dave", and "Will". A sixth scheduled participant, "Jones", did not actually join the HIV management video conference and hence is listed in italic type on the display 26. At the point in time shown in FIG. 10, "Dave" and "Will" have not yet completed entry of their blood pressure readings. Additionally, a request indicator 120 indicates "Will" has requested the floor of the video conference, presumably to ask a question about the blood pressure measurement.

Figure 11:
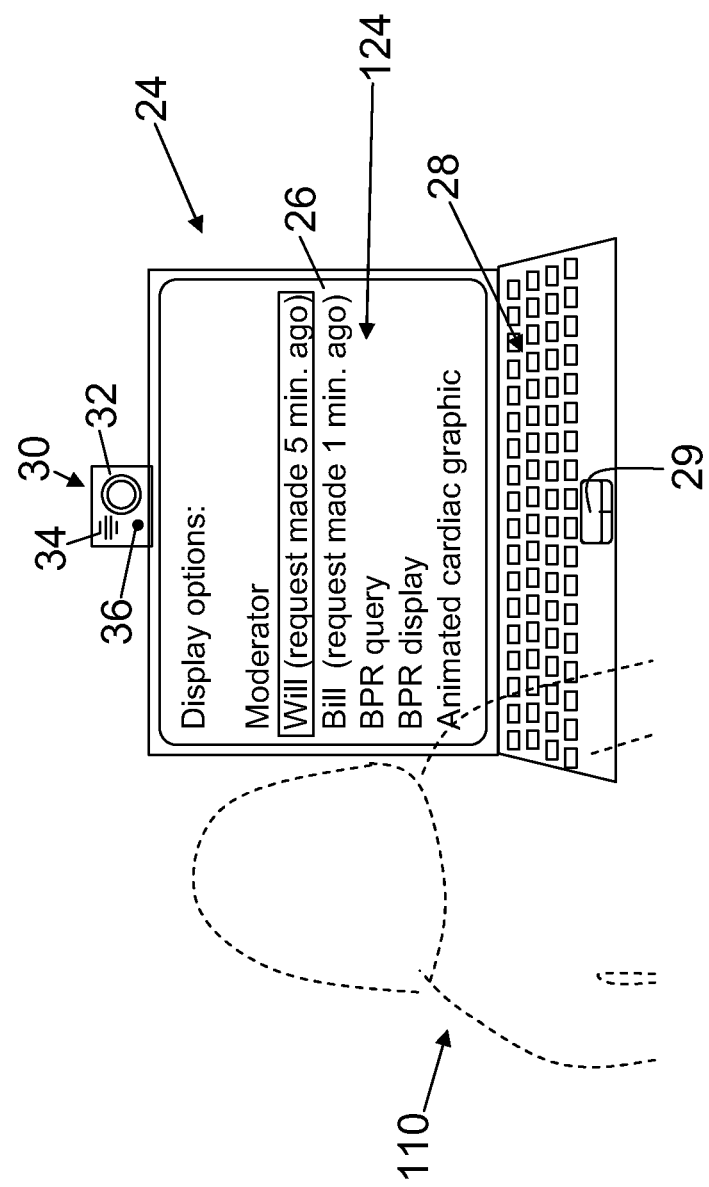

FIG. 11 shows a snapshot of the HIV management video conference from the viewpoint of the moderator 110, but taken a few seconds after the snapshot shown in FIG. 10. At the point in time of FIG. 11, the moderator 110 has switched her view (for example, using appropriate operations of the keyboard 28 or mouse pad 29) to switch to a "Display options" menu 124. This menu 124 provides the moderator with functionality to control what is displayed to participants and viewers of the HIV management video conference. For example, previous FIG. 9 showed "Moderator" and "BPR query" (i.e., blood pressure query) windows. As shown in FIG. 11, the moderator 110 is in the process of switching the video conference display to show "Will" so that he can ask his question. The menu 124 of FIG. 11 also shows that "Bill" has asked a question, but after "Will"—hence, the moderator 110 is about to turn the floor over to "Will" to ask his question first.

Figure 12:
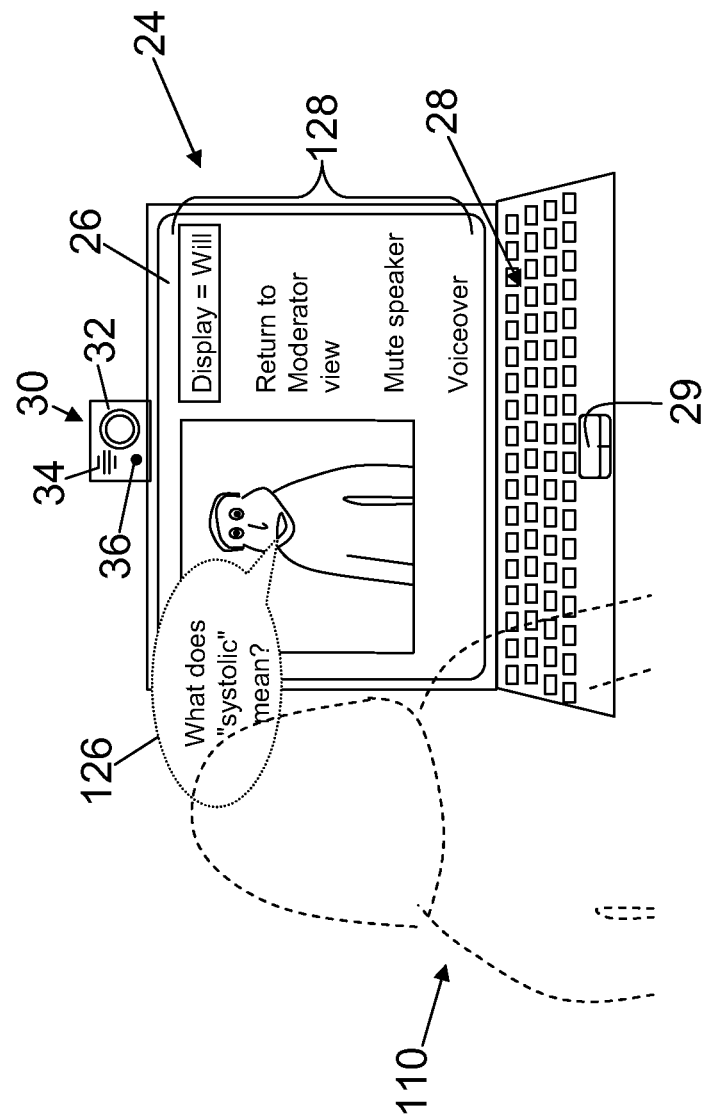

FIG. 12 shows a snapshot of the HIV management video conference from the viewpoint of the moderator 110, but taken a few seconds after the snapshot shown in FIG. 11. At the point in time of FIG. 12, the floor has been turned over to "Will" and "Will" is asking his question, which corresponds to the audio portion "What does 'systolic' mean?" 126. The image and voice of "Will" are suitably provided as recorded audio/video content generated by the camera 61 disposed in the residence of "Will" and transmitted to the moderator via the Internet 14.

In the illustrated centrally controlled embodiment, this recorded audio/video content is first transmitted to the medical server 10, and then relayed from the medical server 10 to the other participants. In a decentralized embodiment, this recorded audio/video content would be transmitted to all other participants and viewers concurrently rather than being relayed through the multi-point control unit 10.

With continuing reference to FIG. 12, an options list 128 is additionally shown on the right-side of the display 26, which options include: the currently highlighted "Display=Will" option; a "return to moderator view" option (likely to be selected after "Will" completes his question so that the Moderator 110 can answer the question posed by "Will"); a "mute speaker" option (advantageously provided so that the moderator can mute out a participant having the floor who starts to vocalize obscenities or the like); and a "voiceover" option (optionally selected after "Will" completes his question instead of selecting the "return to moderator view" option, such that the moderator's answer comes across verbally while "Will" continues to be displayed to the moderator 110 and other participants).

It will be appreciated that the illustrated portion of the illustrative HIV management video conference is an example of a moderated video conference using the illustrative multi-point control unit 10. The moderator may be given additional, fewer, or different controls, and the moderator's user interface may have different layouts or arrangements of options. A moderated video conference has the advantage of allowing personal interactions, but in a controlled manner. For example, in some embodiments, a delay of a few seconds is interposed between the moderator's audio/video at the computer 24 and that audio/video seen by the participants. This delay allows the moderator to edit out, "bleep out", or otherwise remove or modify improper language or unacceptable audio or video content.

Moreover, the moderator 110 can provide additional added content—for example, FIG. 11 shows in the display options the "BPR display", which would show the blood pressure readings of all participants. It is envisioned that such a display would engender competitive motivation amongst the participants—each time the HIV management video conference was conducted, the participants would compete with each other to have the lowest blood pressure reading. Similarly, one can envision a weight loss support group in which the participant's weights are entered and compared. To avoid embarrassing underachieving participants, the moderator might elect to identify the winning participant (e.g., the participant with the lowest blood pressure or with the lowest weight) without identifying other, less impressive, results.

As another example of moderator-added content, FIG. 11 shows that the moderator 110 has the option of displaying an animated cardiac graphic, for example showing a beating heart. Such an animated graphic is readily inserted by inserting pre-recorded video of the beating heart into the output audio/video data stream output by the multi-point control unit 10. Other contemplated moderator-added content may include, for example, a static image, a static image on which the moderator 110 can overlay writing, inserted pre-recorded streaming video, or so forth.

Although a moderated video conference has certain advantages, it also has certain disadvantages. For example, end-users who have a common medical condition or situation such as AIDS, an impending surgical procedure, or so forth may be inhibited in their communication by the presence of a moderator who does not share their condition or situation. Moreover, a moderated video conference occupies the time of a moderator who typically has certain technical or medical skills. A moderated video conference usually is pre-scheduled, since the moderator must be available at the time of the video conference. Alternatively, the first end-user to initiate a video conference can be designated as the moderator—however, this requires that the end-user have the technical skill to perform video conference moderating functions such as switching video sources and so forth.

With reference to FIG. 13, an illustrative unmoderated video conference is described. FIG. 13 depicts a point in time in such an unmoderated video conference. The unmoderated video conference includes video display windows for each participant: "Will", "Jill", and "Bill", and also includes presently unused display windows for "Barry" and "Dave" who are not currently participating. The display shown in FIG. 13 is for "Bill"—accordingly, the caption for that window is "You (Bill)" and that window shows the content recorded locally by the camera 30 located in the residence of "Bill". Optionally, the window showing "Bill" can be omitted since "Bill" does not need to see himself. Indeed, in an ordinary conversation "Bill" does not see himself. However, including the window showing "Bill" on the television viewed by "Bill" advantageously lets "Bill" see how he appears to the other participants. The remaining windows for "Will" and "Jill" show streaming video of "Will" and "Jill" respectively received over the Internet 14. In the approach of FIG. 13, all participants are shown simultaneously in separate windows. The participant's voices are suitably blended together (i.e., superimposed upon each other) by the videoconferencing module 70 of FIG. 4 operating at each residence, or by signal processing operating at the multi-point control unit 10 if centralized control is used. Accordingly, there is no need for any particular participant to have the floor—rather, all participants are viewed simultaneously, and As indicated by on-screen text 130, the end-user "Bill" can exit the video conference at any time by pressing the <ESC> key on his handheld remote controller 60.

The unmoderated video conference shown in FIG. 13 has the advantage of eliminating the need to designate any given person as having the floor, and allowing a setting close to that of an ordinary in-person conversation. However, the number of participants is limited by the display real estate of the television 50—for example, if ten participants are to be included, each individual participant will be displayed relatively small.

With reference to FIGS. 14 and 15, another approach for an unmoderated video conference is illustrated. In this arrangement, a single video window is provided, which at the instant in time shown in FIG. 14 is showing "Will". A notation 134 indicates who is presently participating, namely "Will", "Bill", and "Jill". In this arrangement, only a single participant is viewed at any given time—accordingly, as shown in FIG. 15 the video conferencing engine 70 includes a current speaker disambiguation engine 140 that determines which participant is currently speaking and hence should be viewed. In the approach of FIG. 15, data streams 142 from each participant are inputs to the current speaker disambiguation engine 140, and the current speaker disambiguation engine 140 passes through a data stream 144 of the participant selected as having the floor. The selection is suitably based on factors such as relative audio signal strength integrated over a time window, analysis of video cues such as movement of the mouth, or so forth.

In some embodiments, the unmoderated video conferences illustrated in FIGS. 13-15 are scheduled for a particular day and time, and the participants join the video conference at the scheduled time, for example using the forums menu of FIG. 8. However, unmoderated video conferences have the advantage of being amenable to unscheduled, ad hoc formation.

FIG. 16 shows a suitable user interface for forming and joining ad hoc video conferences. In the approach of FIG. 16, each video conference is assigned a "channel". The channels are supported concurrently, for example using frequency domain multiplexing, time-domain multiplexing, or the like. The available channels are shown in an "Ongoing forums channel guide" 150 shown on the television 50 responsive to a suitable user selection made by the end-user via the handheld remote controller 60. Each entry includes the name of the video conference (e.g., "HIV support group") and the number of current participants (e.g., three current participants for the "HIV support group"). If the end-user wants to join the "HIV support group", he or she selects that video conference from the "Ongoing forums channel guide" 150 and that end-user is added in an ad hoc manner to the video conference.

As further shown in FIG. 16, the "Diabetics support group" does not list any current participants, but instead lists "1 person waiting". That is, one person has indicated that he or she wants to participate in the "Diabetics support group" but since no one else is participating there is no ongoing video conference. If the end-user selects to participate in the "Diabetics support group" then the waiting person is notified, and both are added to the "Diabetics support group" to initiate that video conference. Similarly, if the end-user elects to participate in the "Weight loss group" which presently has no persons participating or waiting (and hence is in an "idle" state), then the end-user will be designated as the "1 person waiting" for the "Weight loss group" and will be notified if and when a second person elects to participate. Preferably, if the waiting person logs off (or otherwise exits) the medical communication system prior to a video conference being set up, then that video conference reverts back to the "idle" state. Similarly, if all current participants exit a given video conference, then that video conference reverts to the "idle" state. In various embodiments, the entries or channels of the "Ongoing forums channel guide" 150 are added or removed by an administrator at the medical server 10, or can be added or removed by individual end-users. In some such latter embodiments, it is contemplated to have no "idle" state, but rather to have the video conference removed from the "Ongoing forums channel guide" 150 when the last participant exits.

The ad hoc joining and exiting of video conferences supported by the "Ongoing forums channel guide" 150 of FIG. 16 advantageously involves little or no intervention by medical professionals. Moreover, these video conferences are available at any time, in some embodiments twenty-four hours a day, so that for example an "insomniacs support group" could be meeting at 3:00 a.m.

In the foregoing, HIV management and other illustrated video conference topics are intended as illustrated examples. In general the topic of the video conference can include any medically related topic, where such topics are intended to encompass both physical and psychological aspects. Thus, a medically related topic may include a vide conference having as its topic general socializing of participants so as to improve the participants' attitude and emotional well being. In such cases, video conference serves as a kind of virtual social outing, but one in which the participants share a medical condition or characteristic and hence are more likely to be willing to share experiences, and are more likely to bond socially.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A medical forum system comprising:
   audio/video interfaces disposed in residences of subjects, each audio/video interface including a consumer electronics device providing audio/video playback capability and a recording device providing audio/video recording capability;
   a distributed medical network which includes a processor disposed in each residence, the processor being operatively coupled with the audio/video interface of that residence, the distributed medical network being configured to perform a video conferencing process;
   the network includes a server which receives an assent or a rejection to be recorded from the processor disposed in the residence of a subject joining a selected video conference and wherein the server is configured for:
   (i) in response to receiving the assent from the subject, providing the audio/video interface of the subject with a participatory connection to the selected video conference by which the subject views the video conference using the playback capability of the consumer electronics device disposed in the subject's residence and participates in the video conference by being recorded using the recording device disposed in the subject's residence, and
   (ii) in response to receiving the rejection from the subject, providing the audio/video interface of the subject with a viewing connection to the selected video conference by which the subject views the selected video conference using the playback capability of the consumer electronics device disposed in the subject's residence but is not recorded using the recording device disposed in the subject's residence, such that the subject views the selected video conference anonymously without participating;

a moderator audio/video interface including audio/video playback capability, audio/video recording capability, and one or more user inputs providing control of at least the video display content of the selected video conference.

2. The medical forum system as set forth in claim 1, wherein the moderator audio/video interface provides control to selectively display (i) a selected participant or (ii) a selected graphic.

3. The medical forum system as set forth in claim 1, wherein the recording device in each residence is integrated with a unit in said residence that further contains the processor disposed in said residence, the unit being separate from and operatively connected with the consumer electronics device.

4. The medical forum system as set forth in claim 1, wherein the distributed medical server network further includes:
 data storage storing pre-recorded audio/video content and care plan schedules corresponding to the residences, the network server being configured to play portions of the pre-recorded audio/video content to processors in selected residences in accordance with the care plan schedules.

5. A medical forum system comprising:
 audio/video interfaces disposed in residences of subjects, each audio/video interface including a consumer electronics device providing audio/video playback capability, a recording device including a video recording lens providing audio/video recording capability, and an automatic lens cover that physically blocks the video recording lens except during audio/video recording; and
 a distributed medical network including a processor disposed in each residence and operatively coupled with the audio/video interface of that residence, the distributed medical network being configured to perform a video conferencing process including:
 receiving an assent or a rejection from the processor disposed in the residence of a subject regarding joining a selected video conference, and
 conditional upon receiving an assent from the subject, physically unblocking the video recording lens of the audio/video recording device disposed in the subject residence and providing the audio/video interface disposed in the subject's residence with a participatory connection to the selected video conference by which the subject views the video conference using the playback capability of the consumer electronics device disposed in the subject's residence and participates in the video conference by being recorded using the recording device disposed in the subject's residence, and
 conditional upon receiving a rejection from the subject, providing the audio/video interface of the subject with a viewing connection to the selected video conference by which the subject views the selected video conference using the playback capability of the consumer electronics device disposed in the subject's residence, but is not recorded using the recording device disposed in the subject's residence, such that the subject views the selected video conference anonymously without being recorded.

6. The medical forum system as set forth in claim 5, wherein the audio/video conference is unmoderated, and the distributed medical network further includes:
 a current speaker disambiguation engine that determines which participant of the video conference should be currently displayed.

7. A medical forum method comprising:
 performing video conferencing over a distributed medical network which includes a processor and an audio/video interface disposed in each residence of a plurality of subjects, each audio/video interface including a consumer electronics device which providing audio/video playback capability and a recording device providing audio/video recording capability, each processor being operatively coupled with the audio/video interface of that residence;
 with a server of the network, receiving an assent or a rejection to be recorded from the processor disposed in the residence of each of a plurality of subjects joining a selected video conference;
 (i) in response to receiving the assent from a first subject, with the server, providing the audio/video interface of the first subject with a participatory connection to the selected video conference by which the first subject views the video conference using the playback capability of the consumer electronics device disposed in the first subject's residence and participates in the video conference by being recorded using the recording device disposed in the first subject's residence, and
 (ii) in response to receiving the rejection from a second subject, with the server, providing the audio/video interface of the second subject with a viewing only connection to the selected video conference by which the second subject views the selected video conference using the playback capability of the consumer electronics device disposed in the second subject's residence and controlling the recording device disposed in the second subject's residence to block the second subject from being recorded, such that the second subject views the first subject during the video conference anonymously, without being recorded and viewed by the first subject, and the first subject is viewed by the second subject but does not view the second subject.

\* \* \* \* \*